United States Patent
Cappelletti

(10) Patent No.: US 10,226,348 B2
(45) Date of Patent: Mar. 12, 2019

(54) ADJUSTABLE MODULAR SPACER DEVICE FOR THE ARTICULATION OF THE KNEE

(71) Applicant: Ava Cappelletti, Cesena (IT)

(72) Inventor: Ava Cappelletti, Cesena (IT)

(73) Assignee: Cossington Limited, Kingston upon Thames, Surrey (GB)

( * ) Notice: Subject to any disclaimer, the term of this patent is extended or adjusted under 35 U.S.C. 154(b) by 0 days.

(21) Appl. No.: 14/534,226

(22) Filed: Nov. 6, 2014

(65) Prior Publication Data

US 2016/0128840 A1    May 12, 2016

(51) Int. Cl.
*A61F 2/38* (2006.01)
*A61F 2/30* (2006.01)
*A61F 2/46* (2006.01)

(52) U.S. Cl.
CPC ............ *A61F 2/3859* (2013.01); *A61F 2/389* (2013.01); *A61F 2/3886* (2013.01); *A61F 2002/30369* (2013.01); *A61F 2002/30448* (2013.01); *A61F 2002/30449* (2013.01); *A61F 2002/30518* (2013.01); *A61F 2002/30537* (2013.01); *A61F 2002/30616* (2013.01); *A61F 2002/30672* (2013.01); *A61F 2002/3863* (2013.01); *A61F 2002/4631* (2013.01); *A61F 2250/0006* (2013.01); *A61F 2250/0064* (2013.01); *A61F 2250/0067* (2013.01); *A61F 2310/00353* (2013.01)

(58) Field of Classification Search
CPC ........ A61F 2/385; A61F 2/3845; A61F 2/384; A61F 2/3836; A61F 2/3859; A61F 2002/3863; A61F 2/389
See application file for complete search history.

(56) References Cited

U.S. PATENT DOCUMENTS

| | | | | |
|---|---|---|---|---|
| 5,370,693 A * | 12/1994 | Kelman | ............. | A61F 2/30724 623/16.11 |
| 6,506,216 B1 * | 1/2003 | McCue | .................. | A61F 2/389 623/20.14 |
| 2011/0112651 A1 * | 5/2011 | Blaylock | ............. | A61F 2/30734 623/20.15 |
| 2013/0073049 A1 * | 3/2013 | Faccioli | .................... | A61F 2/38 623/20.21 |
| 2015/0134068 A1 * | 5/2015 | Leonard | ................ | A61F 2/3886 623/20.27 |
| 2016/0106552 A1 * | 4/2016 | Cardamone | ............... | A61F 2/28 623/23.41 |

* cited by examiner

Primary Examiner — Suba Ganesan
(74) Attorney, Agent, or Firm — Themis Law

(57) ABSTRACT

A knee spacer device configured to be implanted temporarily at the joint area between the tibia and femur of a patient to replace an infected joint prosthesis and to maintain the size or spaces of the patient's joint area before implanting a new prosthesis includes a tibial unit and a femoral unit.

18 Claims, 4 Drawing Sheets

ADJUSTABLE MODULAR SPACER DEVICE FOR THE ARTICULATION OF THE KNEE

FIELD OF THE INVENTION

The present invention concerns a knee spacer device, that is, a device intended to be implanted temporarily at the joint area between the tibia and femur of a patient to maintain the dimensions of such a zone.

BACKGROUND OF THE INVENTION

As it is known, sometimes it is necessary to temporarily remove joint prostheses, for example as a result of the onset of infections in the respective implant area. Moreover, an infected prosthesis or a prosthesis extracted from an infected area cannot be immediately replaced with a new prosthesis, but one must first treat and eliminate the infection with suitable antibiotic drugs.

It should then be noted that during the period required for the antibiotic treatment, the joint space wherein a new joint prosthesis is to be implanted must, of course, be kept unchanged, so as to prevent the shortening of the tissues, the atrophy of the joint and the loss of muscle tone.

In this regard, spacer devices are used, which are intended to be temporarily implanted at the joint area of a patient for replacing a prosthesis and for maintaining the size of the joint area itself before reimplanting a second prosthesis.

The spacer device has the function of maintaining the joint spaces as well as curing the bone infection by releasing amounts of antibiotic in the infected area. As regards the second function now indicated, the spacer can treat the on-going infection by releasing antibiotic in a targeted manner and in infinitesimal quantities, while the application of even high doses of antibiotic, but with methods that do not involve the use of spacers, such as washing the infected area with solutions of high-dose antibiotics, does not allow obtaining the same results.

In fact, studies carried out in the field have revealed that the bone tissue absorbs in a concentrated manner all the (even a few) antibiotic molecules daily released by the spacer. This naturally occurs if the antibiotic is released by the spacer in contact with or near the bone tissue, in which case the amount of antibiotic reaches locally the effective concentration to eradicate the infection. For this reason, it is essential that the spacer extends across the whole infection area, this meaning that if the infected prosthesis is a long prosthesis, a long spacer will be used and, whether the infected prosthesis is of the short type, a short spacer will be used. Should a short spacer be placed where a long prosthesis was previously implanted, part of the bone would not be treated with antibiotic, in this way letting bacteria proliferate.

Spacer devices are usually made of bone cement and with the appropriate size, extemporaneously or prior to their positioning, which greatly increases the duration of the implant operation and also sometimes involves the use of toxic substances.

Pre-formed spacer devices have also been proposed, which cannot be adapted from patient to patient, with the obvious consequence that, in most cases, it is very difficult to guarantee patients a good mobility of the joint before reimplanting the definitive prosthesis.

SUMMARY OF THE INVENTION

An object of the present invention is to provide a new knee spacer device.

Another object of the present invention is to provide a knee spacer device that allows effective adjustments in the implant area.

Another object of the present invention is to provide a knee spacer device which suitable for self-adjusting to the respective implant area.

Another object of the present invention is to provide a new spacer device that can be implanted in a very quick and easy manner.

In accordance with an aspect of the invention a device according to claim 1 is provided.

In accordance with an aspect of the invention a method according to claim 17 is provided.

The dependent claims refer to preferred and advantageous embodiments of the invention.

BRIEF DESCRIPTION OF THE DRAWINGS

Other features and advantages of the invention will be more evident from the description of an embodiment of a device, shown by way of example in the accompanying drawings wherein.

In the accompanying drawings, equal parts or components are identified by the same reference numbers.

DETAILED DESCRIPTION OF EMBODIMENTS OF THE INVENTION

Figure 1:
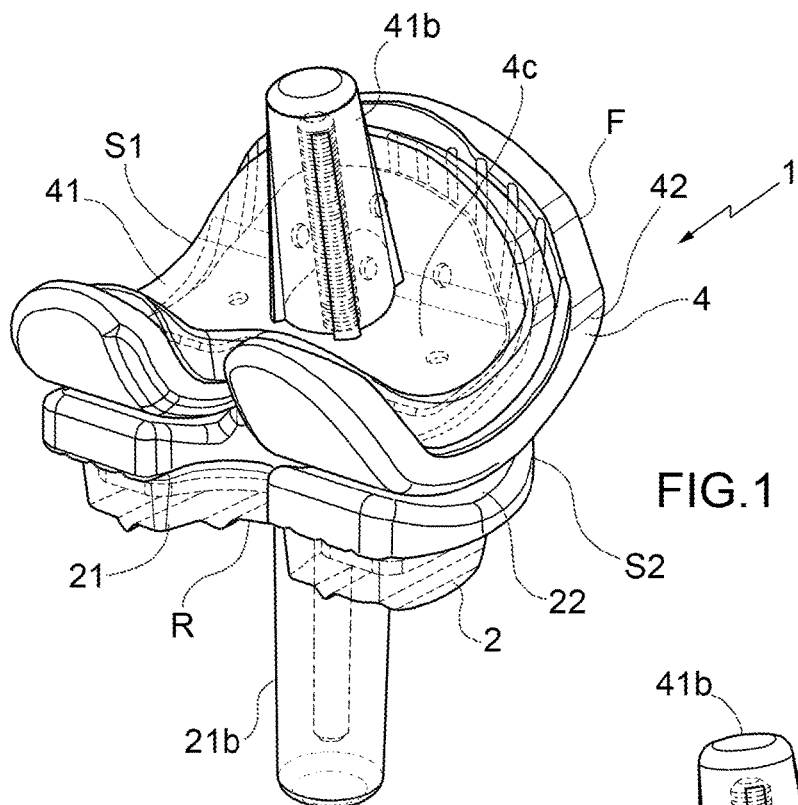
FIGS. 1 and 2 are perspective views from respective sides and with parts in transparency of a spacer device according to the present invention.
Figure 2:
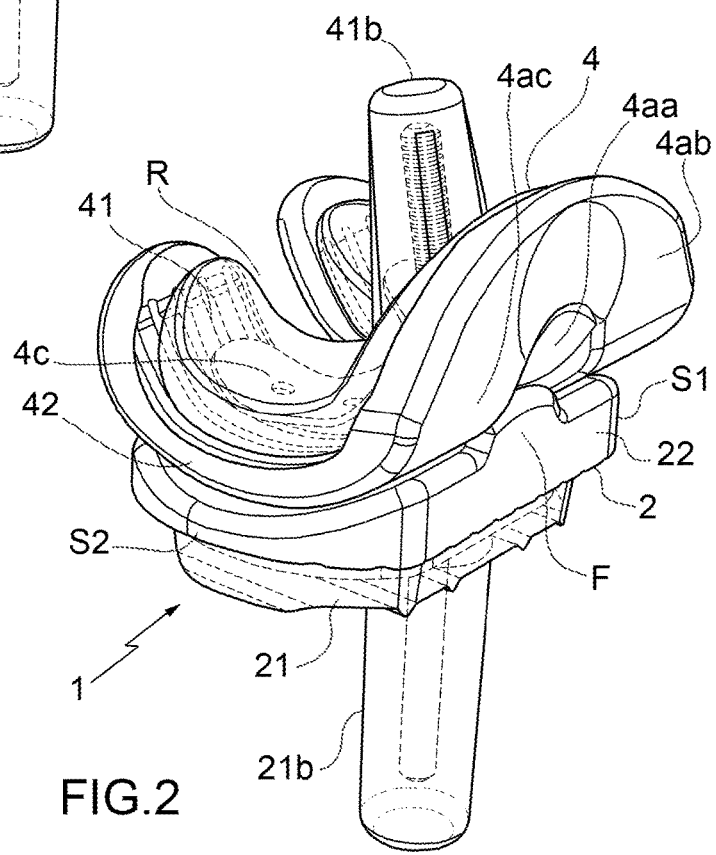
Figure 3:
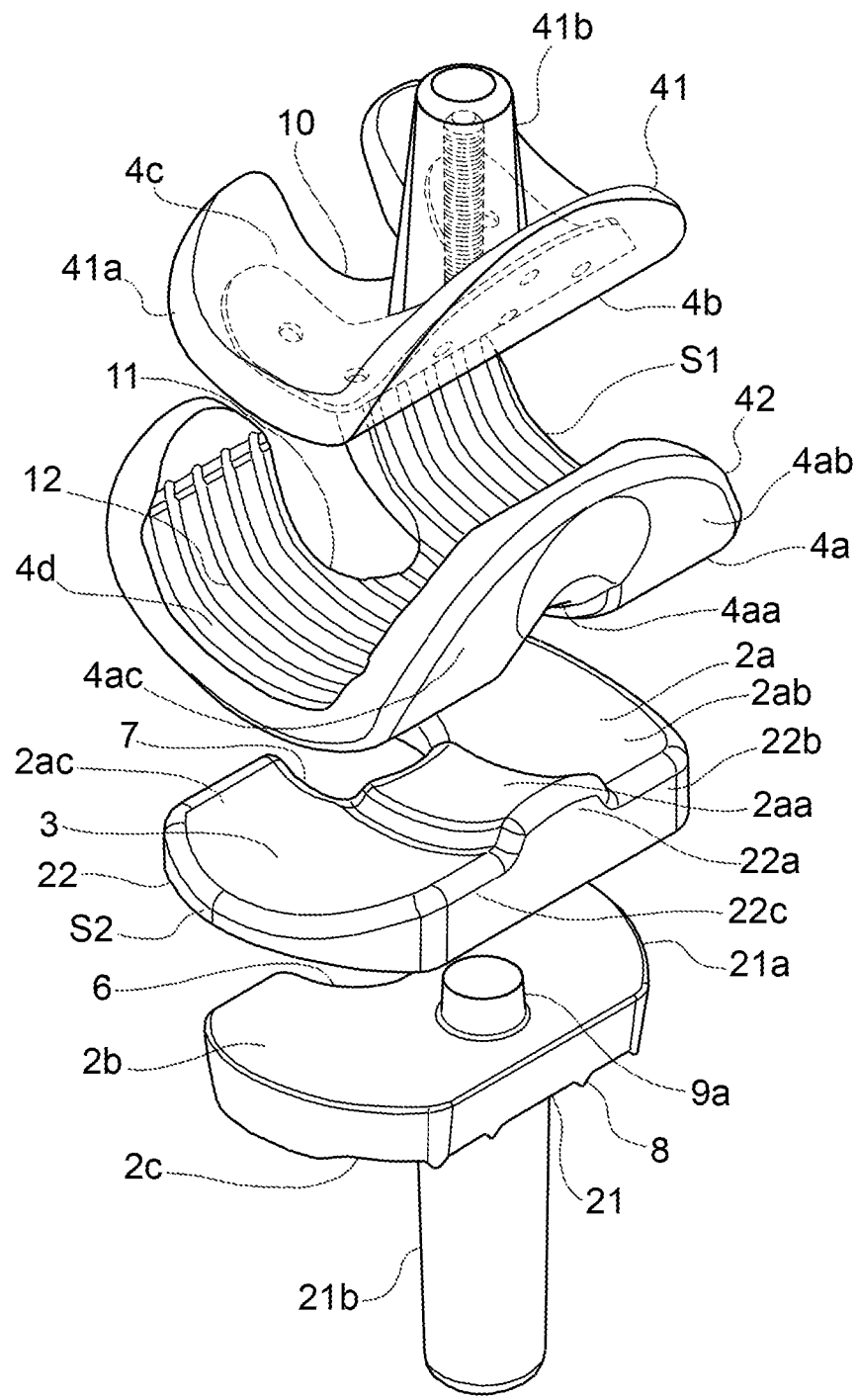
FIG. 3 is a perspective view slightly from above, exploded and with parts in transparency of the device of FIG. 1.
Figure 4:
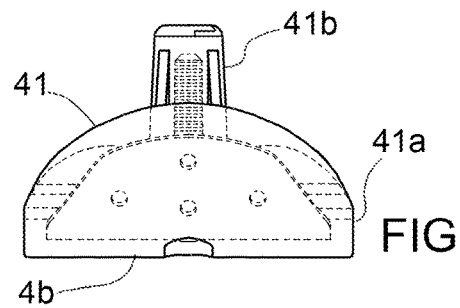
FIGS. 4 and 5 are a front view and a cross-section view of a first femoral component of a device according to the present invention.
Figure 5:
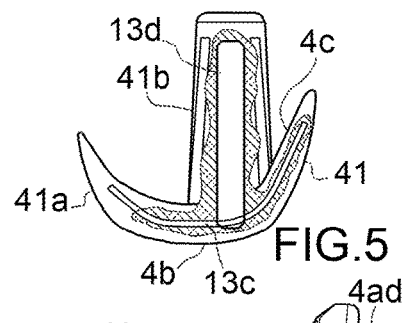
Figure 6:
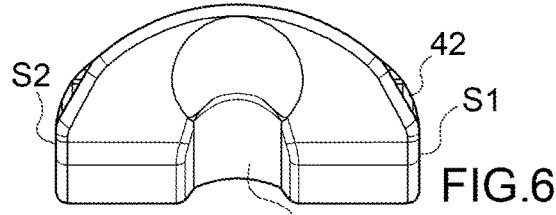
FIGS. 6 and 7 are a front view and a side view of a second femoral component of a device according to the present invention.
Figure 7:
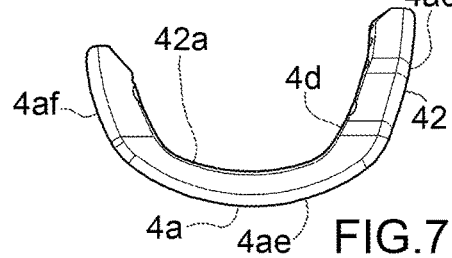
Figure 8:
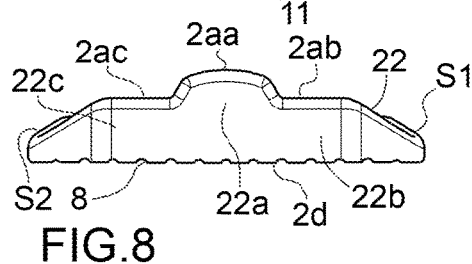
FIGS. 8, 9 and 10 are a front view, a side view and a sectional view, respectively, of a second tibial component of a device according to the present invention.
Figure 9:
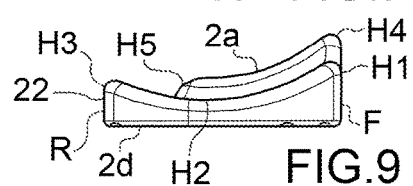
Figure 10:
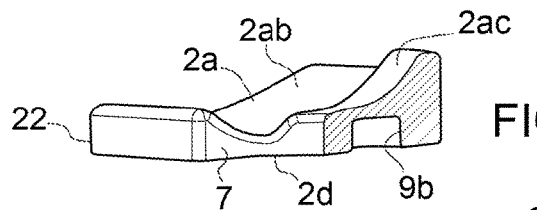
Figure 11:
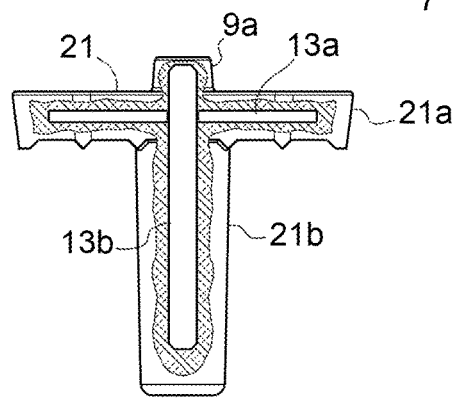
FIGS. 11 and 12 are a front view and a cross-section view of a first tibial component of a device according to the present invention.
Figure 12:
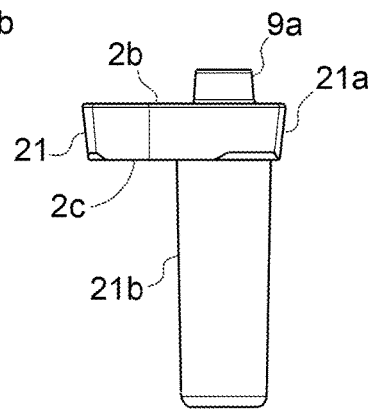

With reference to FIGS. 1 to 12, a knee spacer device 1 according to the present invention is shown, in particular an improved modular adjustable spacer device, if desired disposable, which is intended to be implanted temporarily at the joint area between the tibia and femur of a patient for the replacement of a knee joint prosthesis, for example infected or extracted from an infected area, and for the preservation of the size or spaces of the patient's joint area before implanting a new prosthesis, in particular after the treatment of the infected area.

In the present invention, there will be indicated as the front F of the device, the part thereof which, in use, is arranged at the front part of the knee wherein it is to be implanted, and as the rear R of the device, the part thereof which, in use, is arranged at the rear part of the knee wherein it is to be implanted. As regards the expressions front or fore end or portion or similar expressions, these indicate the ends of a component of the device proximal to the front F and distal from the rear R, while the expressions rear end or portion or similar expressions indicate the ends of a component of the device proximal to the rear R and distal from the front F.

More particularly, the spacer device 1 comprises a tibial unit 2 intended to be fixed to the tibia of a patient and having a first upper, in use, joint surface 2a substantially curved or ramp-shaped delimiting a substantially concave sliding seat 3.

The spacer device is then provided with a femoral unit 4 intended to be fixed to the femur of a patient and provided with a first lower, in use, joint face 4a substantially convex and intended to be positioned in the sliding seat 3 for the sliding engagement of the first upper joint surface 2a, thereby allowing for the joint, if desired a mutual angular or roto-translational displacement between tibial unit 2 and femoral unit 4 and hence, once the device has been implanted, between the tibia and the femur.

Moreover, the tibial unit 2 may comprise a first component 21 fixable to the tibia and distal from the first joint surface 2a, as well as a second component 22 adjustably fixable to the first component 21 in a plurality of operational positions and delimiting the first joint surface 2a, more particularly delimiting the entire first joint surface 2a. In alternative or in addition to this, the femoral unit 4 comprises a first component 41 fixable to the femur and distal from the first joint face 4a, as well as a second component 42 adjustably fixable to the first component 41 in a plurality of operational positions and delimiting the joint face 4a, more particularly delimiting the entire first joint face 4a.

In substance, the second tibial component 22, if provided, constitutes the component of the tibial unit 2 in (sliding or roto-translation) contact with the femoral unit 4 or with the second femoral component 42 of the latter, while the first tibial component 21 is fixed to the tibia and distal and not in contact with the femoral unit 4; moreover, the second tibial component 22 is not intended to come into contact with the tibia. As regards, instead, the second femoral component 42, if such a component is provided, it constitutes the component of the femoral unit 4 in (sliding or roto-translation) contact with the tibial unit 2 or with the second tibial component 22 of the latter, while the first femoral component 41 is fixed to the femur and distal and not in contact with the tibial unit 2; moreover, the second femoral component 42 is not intended to come into contact with the femur.

In the case wherein the tibial unit 2 comprises a first tibial component 21 fixable to the tibia as well as a second tibial component 22 adjustably fixable to the first tibial component 21, the first tibial component 21 may include a base portion 21a delimiting a second intermediate surface 2b, optionally substantially flat, facing towards the second tibial component 22 and a third connection surface 2c, optionally substantially flat, opposite to the second surface 2b and further comprises a first stem 21b, optionally removable, for example connectable by screwing to the base portion 21a, which rises from the third connection surface 2c of the base portion 21a and is intended to be implanted into the tibia of a patient. The second tibial component 22, instead, delimits on one side the first upper joint surface 2a and, on the other side, a fourth intermediate surface 2d intended to be abutted to and fixed against the second intermediate surface 2b of the first tibial component 21. The first stem 21b extends, in use, in a direction substantially longitudinal with respect to the tibial bone of the patient in which it is to be implanted.

If desired, the base portion 21a of the first tibial component 21 is substantially C-shaped and delimits a first channel 6 passing and extending from the second intermediate surface 2b to the third connection surface 2c, while the second tibial component 22 is substantially C-shaped and delimits a second channel 7 extending from the first joint surface 2a to the fourth intermediate surface 2d and is substantially aligned, in use, to the first channel 6.

The first joint surface 2a may include, from a side S1 to the other S2 of the device 1, a raised intermediate part 2aa, as well as two lowered lateral parts 2ab, 2ac placed one opposite to the other with respect to the intermediate part 2aa. To this end, the second tibial component 22 may be provided with an intermediate section with a greater thickness 22a, as well as two lateral sections with a lower thickness 22b, 22c placed one opposite to the other with respect to the intermediate section 22a. In this case, the second channel 7 may be delimited between a rear end of the raised section 22a and rear end lengths of the two lowered sections 22b, 22c. The raised intermediate part 2aa extends longitudinally to the sagittal plane of the knee.

The level or height, in use, of the first joint surface 2a, that is to say the distance of the joint surface 2a from the fourth intermediate surface 2d, may also present a maximum H1 at the front F of the device 1, thus decreasing gradually up to a minimum H2, at a central area and then increasing until reaching a level H3 greater than H2, but smaller than H1 at the rear R. If there are provided a raised intermediate part 2aa and two lowered lateral parts 2ab, 2ac, then the level of the lowered lateral parts 2ab, 2ac follows the pattern now described, while the raised intermediate part 2aa has a maximum level H4 at the front F of the device 1, greater than H1, and thus gradually decreases to a minimum H5, greater than H2, if desired without providing for a terminal section of an increasing height corresponding to that between H2 and H3 of the lowered lateral parts 2ab, 2ac.

A device according to the present invention may then comprise fixing means between the first component 21, 41 and the second component 22, 42 of the same unit (tibial or femoral), which include a first position or rest condition, wherein they connect without fixing the first component 21, 41 and the respective second component 22, 42, and a second position or fixing condition, wherein they fix in a position of the plurality of operational positions the second component 22, 42.

The fixing means may, for example, comprise at least one adhesive layer, such as bone cement between the first component 21, 41 and the second component 22, 42, which layer has a predetermined time of curing or solidification. The adhesive layer is initially intended to take hold or adhere on one side with the first component 21, 41 and, on the other, with the second component 22, 42 of the same unit (tibial or femoral), so as to connect without fixing the first 21, 41 and the second component 22, 42, as well as to harden or solidify successively so as to fix the second component 22, 42 in a position of the plurality of operational positions, so that it is possible to adjust the relative position between the first 21, 41 and respective second 22, 42 component in the period of curing or solidification of the adhesive layer.

In this regard, the second component 22, 42 may be moved with respect to the first component 21, 41 along a first front F-rear R direction, along a second direction from one side S1 to the other S2 and/or along a third direction orthogonal to the first and second direction, that is to say a direction orthogonal to the intermediate surfaces 2b, 2d.

The second intermediate surface 2b of the first tibial component 21 or the fourth intermediate surface 2d of the second tibial component 22 may then present at least one rough or jagged area 8, for example notched, in which, in use, there is provided or reported the adhesive layer, such as a layer of bone cement intended to take hold or adhere on one side with the first tibial component 21 and, on the other, with the second tibial component 22 for fixing them together.

Moreover, the device may then comprise reference means for the guided positioning with unstable constrain of a second component 22, 42 on the other component 21, 41 of the same unit (tibial or femoral), which are intended to allow positioning initially the second component 22, 42 on the other component 21, 41 without, however, locking them in place and without hindering the displacement of the second component 22, 42 in the plurality of operational positions, after which the fixing means are applied and when these are brought from the first to the second condition, the two components 21, 22 or 41, 42 are fixed in position. In this regard, from the first tibial component 21 or from the second tibial component 22, or rather from the second intermediate surface 2b or from the fourth intermediate surface 2d of the latter, a pin component 9a may extend, while in the other between the second tibial component 22 and the first tibial component 21, or rather in the other between the fourth intermediate surface 2d and the second intermediate surface 2b of the latter, at least one guided positioning recess 9b of the pin component 9a is formed. If desired, the engagement between the pin component 9a and positioning recess 9b is loose, that is to say that the pin component 9a has a width smaller than the recess 9b. The pin component 9a as well as the corresponding recess 9b, furthermore, may also be substantially cylindrical or hemispherical.

If the femoral unit 4 comprises a first femoral component 41 fixable to the femur as well as a second femoral component 42 adjustably fixable to the first femoral component 41, the first femoral component 41 presents a main part 41a delimiting a second intermediate face 4b facing the second femoral component 42 and a third connection face 4c opposite the second face 4b and also comprises a second stem 41b, also removable if desired, for example connectable by screwing, which rises from the third connection face 4c of the main part 41 and is intended to be grafted into the femur of a patient. The second femoral component 42 on one side delimits the first lower joint face 4a and, on the other side, a fourth intermediate face 4d intended to be abutted against the second intermediate face 4b of the first femoral component 41. If desired, the second intermediate face 4b and the fourth intermediate face 4d are substantially complementary.

The main part 41a of the first femoral component 41 may also be substantially C-shaped and delimit a third channel 10 extending from the second intermediate face 4b to the third connection face 4c, while the second femoral component 42 is substantially C-shaped delimiting a fourth channel 11 extending from the first joint face 4a to the fourth intermediate face 4d and substantially aligned with the third channel 10. In use, the channels 6, 7, 10 and 11 are substantially aligned or one after the other, so as to define a main rear light of the device.

Moreover, the main part 41a of the first femoral component 41 as well as the second femoral component 42 comprise a plate-like body substantially curved with convexity facing the tibial unit 2 and, in such a case, the first femoral component 41 is, in use, housed within a housing seat 42a delimited by the second femoral component 42 or rather by the fourth intermediate face 4d thereof.

The first joint face 4a may present a hollow central band 4aa, in use intended to slidably engage the raised intermediate part 2aa of the tibial unit, as well as two lateral enlarged bands 4ab, 4ac placed one on the opposite side to the other with respect to the hollow band 4aa and each intended to slidably engage a respective lowered part 2ab, 2ac. In such a case, the fourth channel 11 may be delimited between a rear end of the hollow central band 4aa and front end parts of the two lateral enlarged bands 4ab, 4ac. The hollow central band 4aa extends longitudinally to the sagittal plane of the knee.

If during the movement of the knee joint the spacer device 1 is subjected to stresses of lateral thrust, the raised intermediate part 2aa holds in place the hollow central band 4aa and thus the femoral element 4, ensuring a correct movement and good stability of the joint itself.

The first joint face 4a may also present a much greater extension in the front F-rear R direction compared to the first joint surface 2a. In this regard, from the front F to the rear R of the device, the first joint face 4a may include three curved sections with convexity, in use, facing the first joint surface and, more particularly, a first slightly curved section 4ad, then a second section 4ae with a curvature greater than the first section 4ad, and then a third slightly curved section 4af with a curvature corresponding to that of the first section 4ad.

More particularly, the radius of curvature of the second section 4ae may be smaller than the radius of curvature of the first joint surface 2a. Such radii of curvature are chosen in such a way as to allow combining each second femoral component 42 with each second tibial component 22 of a kit according to the present invention, which will be better described hereinafter.

If a hollow central band 4aa and two lateral enlarged bands 4ab, 4ac are provided, then the two lateral enlarged bands 4ab, 4ac follow the pattern now described, while the hollow central band 4aa presents a first slightly curved section 4ad and a second section 4ae, but, if desired, does not comprise a third section 4af.

The second intermediate face 4b of the first femoral component 41 or the fourth intermediate face 4d of the second femoral component 42 may include at least one rough or jagged area 12 and there is provided a layer of bone cement at the rough or jagged area 12 intended to take hold or adhere on one side with the first femoral component 41 and, on the other, with the second femoral component 42 for fixing them together.

The first tibial 21 or femoral 41 component, as well as the second tibial 22 or femoral 42 component are pre-formed and made of biologically compatible material, capable of being additivated and/or additivable with one or more pharmaceutical products, active and/or therapeutic ingredients intended to be released in the tissues of the patient adjacent to the device or rather in the above-mentioned joint area of a patient so as to treat the infection of the bone ends of the tibia and femur.

The biologically compatible material of the spacer device according to the invention may be porous, in particular include interconnected or non-interconnected pores.

The materials for the components of a spacer device according to the present invention can be chosen among: metals, metal alloys, metal-organics, ceramic, glass, plastic materials or a combination thereof.

The plastic materials can be selected among thermoplastic polymers, such as acrylic resins, polyethylene, polypropylene, polyester, etcetera, thermoformable polymers and other similar materials.

In one version of the invention, the biologically compatible material of which the components 21, 22, 41 and 42 of the spacer device 1 are made comprises a bone cement or polymethylmethacrylate.

The pharmaceutical products, active and/or therapeutic ingredients may include antibiotics, antiseptics, bacteriostatics, bactericides, antimycotics, chemotherapeutics, for example, gentamicin, vancomycin, etcetera, or other active ingredients.

The material of the spacer device, being porous, may be additivated with one or more pharmaceutical products, active and/or therapeutic ingredients at the production site, or subsequently by the physician when used on the patient, for example by impregnation.

Moreover, within the components of the device, in particular within the first tibial component 21 and/or the first femoral component 41, a stiffening core 13a, 13b, 13c, 13d, for example metallic, embedded within a biologically compatible material as mentioned above can be provided.

The device may then comprise removable connection means, such as clips between the tibial unit 2 and the femoral unit 4, which clips can serve in particular to limit the relative displacements of such units transversely to a front F-rear R direction or from a side S1 to the other S2 during bone implant operations.

Figure 13:
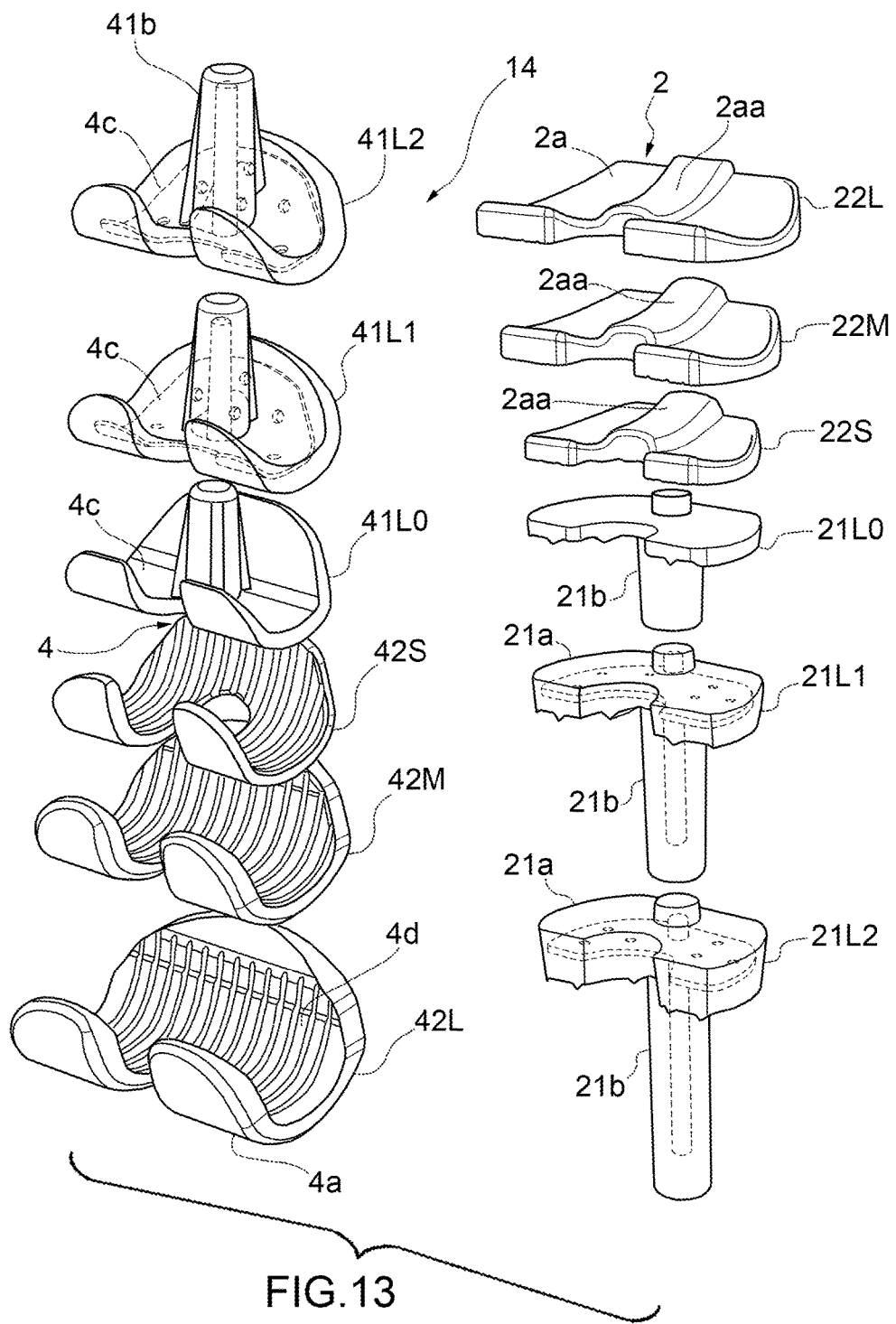
FIG. 13 shoes the components of a kit for making a spacer device according to the present invention.

According to the present invention, a kit 14 (see FIG. 13) is also provided for the realisation of a knee spacer device according to the present invention, comprising at least two first components 21, 41 of different dimensions and/or at least two second components 22, 42 of different dimensions.

The kit 14 could, for example, comprise a tibial unit 2 provided with a first small tibial component 21L0, a first medium tibial component 21L1 and a first large tibial component 21L2, as well as a second small tibial component 22S, a second medium tibial component 22M and a second large tibial component 22L. The first tibial components 21L0, 21L1, 21L2 are usable in combination with any one of the second tibial components 22S, 22M and 22L depending on the needs.

In alternative or in addition to this, the kit 14 could, for example, comprise a femoral unit 4 provided with a first small femoral component 41L0, a first medium femoral component 41L1 and a first large femoral component 41L2, as well as a second small femoral component 42S, a second medium femoral component 42M and a second large femoral component 42L. The first femoral components 41L0, 41L1, 41L2 are usable in combination with any one of the second femoral components 42S, 42M and 42L depending on needs.

To facilitate modularity in a kit according to the present invention, the raised intermediate parts 2aa of all the second tibial components 22 have the same dimensions and the hollow central bands 4aa of all the second femoral components 44 have the same dimensions.

Such modularity of the spacer device 1 allows adapting the latter to the anthropomorphic measurements of the femoral and tibial ends of a patient.

For implanting in a knee a spacer device with a method according to the present invention, the surgeon first decides which components to use, after which the first tibial component 21 or the first stem 21b of the latter is implanted in the tibia and the first femoral component 41 or the second stem 41b of the same in the femur, and therefore the fixing means are applied, for example, an adhesive layer is applied, such as a layer of bone cement on the second intermediate surface 2b and on the second intermediate face 4b. At this point, with the fixing means in the first rest condition, for example before the curing or polymerisation of the adhesive layers, the second tibial component 22 is arranged on the first tibial component 21 and, more particularly, the fourth intermediate surface 2d on the second intermediate surface 2b as well as the second femoral component 42 in abutment against the first tibial component 41 and, more particularly, the fourth intermediate face 4d against the second intermediate face 4b.

Subsequently, and still before the curing or polymerization of the adhesive layers, the tibia and femur are mutually displaced so as to reduce the joint, that is to say so as to straighten, in fact, the leg and bring the first joint face 4a within the sliding seat 3 for the sliding engagement of the first joint surface 2a.

In this way, the tibial unit 2 and the femoral unit 4 are brought in interference and, thanks to the fact that the adhesive layer is not yet polymerized, in the case wherein reciprocal tensions or stresses between the units 2 and 4 remain, the latter, in fact, self-centre or otherwise the relative position of the same is adjusted automatically, thus obtaining in this way a physiological collimation or a natural alignment neutralizing, in fact, the risk of wrong placements, which occur very frequently when using traditional spacers which present medium dimensions and are little anatomical. Then, when the fixing means are brought into the second position, for example during the curing of the adhesive layers, the spacer device is properly implanted. In this regard, thanks to the structures of the tibial 2 and femoral 4 units of a device according to the present invention, it is possible to obtain a self-adjustment of the relative position of the same along three different axes or directions, that is to say a first front F-rear R direction, a second direction from one side S1 to the other S2 and/or a third direction orthogonal to the first and second direction, that is to say a direction orthogonal to the intermediate surfaces 2b, 2d along which the two tibial 2 and femoral 4 units, and hence the first joint surface 2a and the first joint face 4a, are moved away or approached.

Moreover, as mentioned above, one could alternatively have only the tibial unit 2 or the femoral unit 4 in two components, in which case it would still be possible to obtain a self-adjustment of the device when straightening the leg.

As will be understood, a spacer device according to the present invention allows for an optimal adjustment or adaptation to the respective implant area and may be implanted in a very quick and easy manner.

Modifications and variations of the invention are possible within the scope of protection defined by the claims.

The invention claimed is:

1. A knee spacer device configured to be temporarily implanted at a joint area between tibia and femur of a patient to replace an infected joint prosthesis and preserve size or spaces of the joint area before implanting a new prosthesis, said knee spacer device comprising:
   a tibial unit configured to be fixed to a tibia of a patient and having an upper, in use, first joint surface substantially curved and delimiting a substantially concave sliding seat; and
   a femoral unit configured to be fixed to a femur of a patient and having a lower, in use, first joint face, substantially convex and configured to be positioned in said sliding seat for sliding engagement with said upper first joint surface, thereby allowing a mutual angular displacement between said tibial unit and said femoral unit,
   wherein said tibial unit comprises:
      a first tibial component adapted to be fixed to the tibia and distal from said first joint surface, and
      a second tibial component that is monolithic and is adapted to be adjustably fixed to the first tibial component in a plurality of operational positions and delimiting said first joint surface, wherein said second tibial component is adjustably fixable to the first component in at least two of the following directions: a first sagittal direction from front to rear of said device, a second transverse direction from one side to another side of said device, and a longitudinal direction orthogonally to said first and said second directions, wherein a reference member extends from one of said first or said second tibial component, and wherein a recess is defined in the other one of said first or said second tibial component, said recess being larger than a maximum width of said reference member, so as to receive said reference member while allowing said reference member to laterally move therein.

2. The device according to claim 1, further comprising an adhesive product disposed between said first tibial component and said tibial second component having a first position or rest condition, in which said adhesive product connects without fixing said first tibial component and said second tibial component, and a second position or fixing condition, in which said adhesive product fixes said second tibial component to said first tibial component in one position of said plurality of operational positions.

3. The device according to claim 2, wherein said adhesive product is disposed as at least one adhesive layer between said first tibial component and said second tibial component, said at least one adhesive layer having a time of curing or solidification, said at least one adhesive layer being adapted initially to take hold or adhere on one side to said first tibial component and on another side to said second tibial component, thereby connecting without fixing said first and said second component, and to subsequently harden or solidify so as to fix said second tibial component in one position of said plurality of operational positions, so that a relative position between said first and said second tibial component is adjustable during a period of curing or solidification of said at least one adhesive layer.

4. The device according to claim 3, wherein said at least one adhesive layer comprises a layer of bone cement.

5. The device according to claim 1, wherein said femoral unit comprises a first femoral component fixable to the femur and distal from said first joint face and a second femoral component adjustably fixable to said first femoral component in the plurality of operational positions and delimiting said first joint face.

6. The device according to claim 1,
wherein said first tibial component has a base portion delimiting a second intermediate surface facing toward said second tibial component and a third connection surface opposite to said second intermediate surface, and further comprises a first stem rising from said third connection surface of said base portion and configured to be implanted in the tibia of a patient, while said second tibial component on one side delimits said first upper joint surface and on another side a fourth intermediate surface intended to be abutted against said second intermediate surface of said first tibial component.

7. The device according to claim 6, wherein said base portion of said first tibial component is substantially C-shaped and delimits a first channel extending from said second intermediate surface to said third connection surface, while said second tibial component is substantially C-shaped and delimits a second channel extending from said first joint surface to said fourth intermediate surface and is substantially aligned with said first channel.

8. The device according to claim 6, wherein said second intermediate surface of said first tibial component or said fourth intermediate surface of said second tibial component has at least one rough or jagged area, and wherein at least one adhesive layer is placed at said at least one rough or jagged area.

9. The device according to claim 1,
wherein said reference member comprises at least one pin component.

10. The device according to claim 1,
wherein said femoral unit comprises a first femoral component adapted to be fixed to the femur and a second femoral component adjustably fixable to the first femoral component, wherein said first femoral component comprises a main part delimiting a second intermediate face facing toward said second femoral component and a third connection face opposite to said second intermediate face, and further comprises a shaft extending from said third connection face of said main part and configured to be implanted in the femur of a patient, and
wherein said second femoral component on one side delimits said first lower joint face and on another side delimits a fourth intermediate face intended to be abutted against said second intermediate face of said first femoral component.

11. The device according to claim 10, wherein said main part of said first femoral component is substantially C-shaped and delimits a third channel extending from said second intermediate face to said third connection face, while said second femoral component is substantially C-shaped and delimits a fourth channel extending from said first joint face to said fourth intermediate face and is substantially aligned with said third channel.

12. The device according to claim 11, wherein said second intermediate face of said first femoral component or said fourth intermediate face of said second femoral component has at least one rough or jagged area, and wherein at least one adhesive layer is placed at said at least one rough or jagged area.

13. The device according to claim 1, wherein at least one of said tibial unit and said femoral unit is made of a biologically compatible material, and wherein said biologically compatible material is porous and adapted to receive one or more pharmaceutical products, active, or therapeutic ingredients.

14. The device according to claim 1, wherein said tibial unit and said femoral unit both have a C-shape,
wherein a raised portion is defined in said tibial unit, said raised portion extending upwardly from said first joint surface across said C-shape to end between arms of said C-shape, and
wherein a recess is defined in said femoral unit, said recess extending within said first joint face across said C-shape and being sized to receive said raised portion,
whereby a mating of said recess with said raised portion provides for a mutual rotation of said tibial unit and said femoral unit.

15. A knee spacer device configured to be temporarily implanted at a joint area between tibia and femur of a patient to replace an infected joint prosthesis and preserve size or spaces of the joint area before implanting a new prosthesis, said knee spacer device comprising:

a tibial unit configured to be fixed to a tibia of a patient and having an upper, in use, first joint surface substantially curved and delimiting a substantially concave sliding seat; and a femoral unit configured to be fixed to a femur of the patient and having a lower, in use, first joint face, substantially convex and configured to be positioned in said sliding seat for sliding engagement with said first upper joint surface, thereby allowing a mutual angular displacement between said tibial unit and said femoral unit, wherein said femoral unit comprises:
  a first femoral component adapted to be fixed to the femur and distal from said first joint face, and
  a second femoral component that is monolithic and is adapted to be adjustably fixed to the first femoral component in a plurality of lateral operational positions and delimiting said first joint face, and wherein said second femoral component is adjustably fixable to the first component in at least two of the following directions: a first sagittal direction from front to rear of said device, a second transverse direction from one side to another side of said device, and a longitudinal direction orthogonally to said first and said second directions.

16. The device according to claim 15, further comprising an adhesive product disposed between said first femoral component and said femoral second component having a first position or rest condition, in which said adhesive product connects without fixing said first femoral component and said second femoral component, and a second position or fixing condition, in which said adhesive product fixes said second femoral component to said first femoral component in one position of said plurality of operational positions.

17. The device according to claim 15,
wherein said first femoral component comprises a main part delimiting a second intermediate face facing toward said second femoral component and a third connection face opposite to said second intermediate face, and further comprises a shaft extending from said third connection face of said main part and configured to be implanted in the femur of the patient, and wherein said second femoral component on one side delimits said first lower joint face and on another side delimits a fourth intermediate face intended to be abutted against said second intermediate face of said first femoral component.

18. A knee spacer device configured to be temporarily implanted at a joint area between tibia and femur of a patient to replace an infected joint prosthesis and for the preservation of size or spaces of the joint area before implanting a new prosthesis, said knee spacer device comprising:

a tibial unit configured to be fixed to a tibia of a patient and having an upper, in use, first joint surface substantially curved and delimiting a substantially concave sliding seat; and a femoral unit configured to be fixed to a femur of a patient and having a lower, in use, first joint face, substantially convex and intended to be positioned in said sliding seat for sliding engagement with said first upper joint surface, thereby allowing a mutual angular displacement between said tibial unit and said femoral unit, wherein at least one between said tibial unit and said femoral unit comprises:

a first component fixable to the tibia or the femur and distal from said first joint surface or from said first joint face, and a second component adjustable in position in relation to the first component in a plurality of directions without intermediate members therebetween and delimiting said first joint surface or said first joint face, said plurality of directions comprising at least two of the following: a first sagittal direction from front to rear of said device, a second transverse direction from one side to another side of said device, and a longitudinal direction orthogonally to said first and said second directions.

* * * * *